United States Patent [19]
Quittmann et al.

[11] Patent Number: 5,534,651
[45] Date of Patent: Jul. 9, 1996

[54] PROCESS FOR PREPARING γ-MERCAPTOCARBOXYLIC ACID DERIVATIVES

[75] Inventors: Wilhelm Quittmann; John McGarrity, both of Visp, Switzerland

[73] Assignee: Lonza Ltd., Gampel/Valais, Switzerland

[21] Appl. No.: 297,756

[22] Filed: Aug. 30, 1994

[30] Foreign Application Priority Data

Sep. 3, 1993 [CH] Switzerland ............................ 2626/93

[51] Int. Cl.$^6$ .................................................. C07C 321/00
[52] U.S. Cl. ............................ 560/15; 560/147; 562/426; 562/506; 562/606
[58] Field of Search ...................... 560/147, 15; 562/506, 562/426, 606

[56] References Cited

U.S. PATENT DOCUMENTS

| | | | |
|---|---|---|---|
| 4,219,562 | 8/1980 | Roman | 424/304 |
| 4,707,491 | 11/1987 | Covey et al. | 514/445 |
| 5,028,725 | 7/1991 | King | 556/113 |
| 5,270,324 | 12/1993 | Zamboni | 514/311 |

FOREIGN PATENT DOCUMENTS

| | | | |
|---|---|---|---|
| 0172371 | 2/1986 | European Pat. Off. | C07D 315/00 |
| 0480717 | 4/1992 | European Pat. Off. | C07D 215/18 |
| 1199276 | 8/1965 | Germany | C07C 6/01 |
| 3801479 | 11/1988 | Germany | C07D 409/06 |

OTHER PUBLICATIONS

Ming–De Wang et al., "Regiospecific Carbonylation and Ring Expansion of Thietanes and Oxetanes Catalyzed by Cobalt and/or Ruthenium Carbonyls", J. Org. Chem., vol. 54, (1989), pp. 20–21.

Adams, Richard D. et al., "Ring Opening and Carbonylation of 3,3–Dimethylthietane Ligands in Ruthenium Carbonyl Cluster Complexes", Organometallics, vol. 11, (1992), pp. 3422–3426.

S. S. Canan Koch and A. R. Chamberlain, J. Org. Chem., (1993), 58, pp. 2725 to 2737.

Stevens et al., Journal of Organic Chemistry, vol. 29, "The Kinetics of Basic Hydrolysis of some γ–lactones and γ–thiolactones in aqueous acetone", 1954, pp. 1996–2003.

*Primary Examiner*—José G. Dees
*Assistant Examiner*—Rosalynd A. Williams
*Attorney, Agent, or Firm*—Fisher, Christen & Sabol

[57] ABSTRACT

γ-Mercaptocarboxylic acids and their derivatives, in particular esters and amides, are prepared from γ-butyrolactones via the corresponding thiolactones. The thiolactones are obtained by reaction of a γ-lactone with thiocarboxylates in polar solvents and are converted by ring opening using nucleophilic reagents, such as, alkali metal alkoxides, into the γ-mercaptocarboxylic acid derivatives. These are intermediates, for example, for the synthesis of leucotriene antagonists.

24 Claims, No Drawings

PROCESS FOR PREPARING γ-MERCAPTOCARBOXYLIC ACID DERIVATIVES

BACKGROUND OF THE INVENTION

1. Field Of The Invention

The invention relates to a process for preparing γ-mercaptocarboxylic acid derivatives from γ-lactones and also new β-substituted γ-thiolactones as intermediates.

2. Background Art

γ-Mercaptocarboxylic acids and their derivatives such as esters and amides are intermediates, for example, in the synthesis of leucotriene antagonists (European Published Patent Application No. 0480717). The known processes for preparing γ-mercaptocarboxylic acid derivatives start, for example, with the corresponding γ-halocarboxylic acid derivatives whose halogen atoms are replaced, by means of nucleophilic substitution using inorganic sulfides or hydrogen sulfides, by the thiol group. It is also possible to use, in place of the halogen compounds, sulfonic acid esters of the corresponding hydroxycarboxylic acid, for example, the mesylates or tosylates, which can also be reacted with organic sulfur compounds, such as, thiocarboxylic acids or their salts, to give the mercapto compounds. All of these processes have the disadvantage that they first require the introduction of an "assistant substituent" (halide, sulfonate) which is subsequently cleaved off again and finally has to be disposed of as waste.

BROAD DESCRIPTION OF THE INVENTION

An object of the invention is to provide a process for preparing γ-mercaptocarboxylic acids and their derivatives which starts with readily available compounds and produces little waste. According to the invention, this object is achieved by the invention process.

Other objects and advantages are set out herein or are obvious herefrom to one skilled in the art.

The objects and advantages of the invention are achieved by the process and compounds of the invention.

The invention involves a process for preparing γ-mercaptocarboxylic acid derivatives of the general formula:

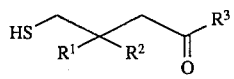

I wherein $R^1$ and $R^2$ are either, independently of one another, hydrogen, $C_1$–$C_6$-alkyl or aralkyl or together are a —$(CH_2)_n$-group having n= from 2 to 5, $R^3$ is hydroxy, $C_1$–$C_6$-alkoxy, cycloalkyloxy, aryloxy, aralkyloxy or —$NR^4R^5$ and $R^4$ and $R^5$ are either, independently of one another, hydrogen, $C_1$–$C_6$-alkyl, cycloalkyl, aryl or aralkyl, or $R^4$ and $R^5$ together are a —$(CH_2)_4$—, —$(CH_2)_5$— or —$(CH_2)_2$—O—$(CH_2)_2$— group, or salts thereof. The process includes reacting a γ-lactone of the general formula:

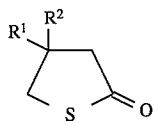

II wherein $R^1$ and $R^2$ are as defined above, with a thiocarboxylate of the general formula:

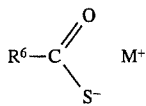

III wherein $R^6$ is a $C_1$–$C_6$-alkyl group and M is an alkali metal, in a polar solvent to give the corresponding thiolactone of the general formula:

IV wherein $R^1$ and $R^2$ are as defined above, and subsequently reacting the thiolactone with a nucleophile of the general formula:

$$R^3H \qquad V$$

wherein $R^3$ is as defined above, or the corresponding anion:

$$(R^3)^- \qquad V'$$

to give the target compound I or a corresponding salt.

Preferably the polar solvent used for the reaction of the γ-lactone with the thiocarboxylate is a polar aprotic solvent selected from the group consisting of dimethyl sulfoxide, sulfolane, N-methylpyrrolidone, N,N-dimethylformamide, N,N-dimethylacetamide and 1,3-dimethyl-3,4,5,6-tetrahydro-2(1H)-pyrimidinone. Preferably the polar solvent used for the reaction of the γ-lactone with the thiocarboxylate is N,N-dimethylacetamide and the reaction is carried out at from 120° to 170° C. Preferably the thiocarboxylate is potassium thioacetate. Preferably a $C_1$–$C_6$-alkanol is used as nucleophile $R^3H$ in the presence of boron trifluoride as the catalyst. Preferably the nucleophile $(R^3)^-$ is the hydroxide ion from an alkali metal hydroxide. Preferably the nucleophile $(R^3)^-$ is the alkoxide ion from a C–$C_6$-alkanol. Preferably the nucleophile $R^3H$ is ammonia. Preferably the nucleophile $R^3H$ used is an amine selected from the group consisting of $C_1$–$C_6$-alkylamines, the cycloalkylamines, the arylamines or the aralkylamines.

The invention also involves the thiolactones of the formula:

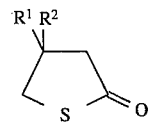

IV' wherein $R^1$ and $R^2$ are as defined above, with the proviso that $R^1$ and $R^2$ are not both simultaneously hydrogen. The thiolactone of formula IV is preferably 5-thiaspiro[2.4]heptan-6-one of the formula:

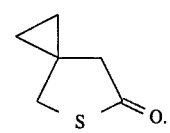

DETAILED DESCRIPTION OF THE INVENTION

It has been found that the readily available γ-lactones of the general formula:

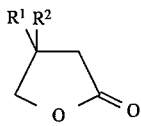 II wherein $R^1$ and $R^2$ are either, independently of one another, hydrogen, $C_1$–$C_6$-alkyl or aralkyl or $R^1$ and $R^2$ together are a —$(CH_2)_n$— group having n as an integer from 2 to 5, can be converted using a thiocarboxylate of the general formula:

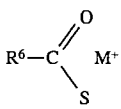 III wherein $R^6$ is a $C_1$–$C_6$-alkyl group or a phenyl group and M is an alkali metal, into the corresponding thiolactones of the general formula:

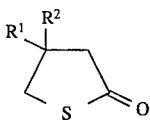 IV and these, by means of reaction with a nucleophile of the general formula:

$R^3H$    V wherein $R^3$ is hydroxy, $C_1$–$C_6$-alkoxy, cycloalkyloxy, aryloxy, aralkyloxy or —$NR^4R^5$, where $R^4$ nd $R^5$ are, independently of one another, hydrogen, $C_1$–$C_6$-alkyl, cycloalkyl, aryl or aralkyl or $R^4$ and $R^5$ together form a —$(CH_2)_4$—, —$(CH_2)_5$— or —$(CH_2)_2$—O—$(CH_2)_2$—chain, or the corresponding anion of the desired γ-mercaptocarboxylic acid of the general formula:

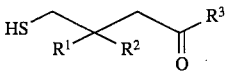 I or esters thereof, give an amide or a salt of this acid.

For the purposes of the invention, $C_1$–$C_6$-alkyl is here, in each case, not only straight-chain primary alkyl groups, i.e., methyl, ethyl, propyl, butyl, pentyl or hexyl, but also all isomeric secondary, tertiary or branched alkyl groups having up to 6 carbon atoms, for example, also isopropyl, sec-butyl, tert-butyl, isobutyl or isopentyl. The same applies to the alkyl component of the groups described here as $C_1$–$C_6$-alkoxy. For the purposes of the invention, cycloalkyl is, in particular, groups having 3 to 6 ring members, for example, cyclopropyl, cyclobutyl, cyclopentyl or cyclohexyl. For the purposes of the invention, aryl is both unsubstituted and substituted aromatic radicals, for example, phenyl, naphthyl, chlorophenyl, tolyl, xylyl or methoxyphenyl; in each case in the form of all possible positional isomers. For the purposes of the invention, aralkyl is aryl-substituted $C_1$–$C_6$-alkyl groups, i.e., in particular groups such as benzyl, 1-phenylethyl, 2-phenylethyl or 3-phenylpropyl.

The γ-lactones of the general formula II are either commercially available (γ-butyrolactone, $R^1=R^2=H$) or can be prepared by known methods [e.g., β,β-dimethyl-γ-butyrolactone, European Published Patent Application No. 172371; for a generally applicable process for preparing optically active β-alkyl-γ-butyrolactone, see also *S. S. Canan Koch and A. R. Chamberlin*, J. Org. Chem., (1993), 58, 2725 to 2737].

Suitable thiocarboxylates (III) are the alkali metal salts of monothioalkanoic acids, in which a $C_1$–$C_6$-alkyl group bears the thiocarboxylate group, and also the alkali metal salts of thiobenzoic acid. Preference is given to using a potassium salt since this is more readily soluble in organic solvents than the corresponding sodium compound. The particularly preferred thiocarboxylate (III) is potassium thioacetate.

The reaction of the lactone with the thiocarboxylate is advantageously carried out in a polar aprotic organic solvent, such as, dimethyl sulfoxide, N-methylpyrrolidone, sulfolane (tetramethylene sulfone), N—N-dimethylformamide, N,N-dimethylacetamide or tetraalkylated ureas, such as, 1,3-dimethyl-3,4,5,6-tetrahydro-2(1H)-pyrimidinone (DMPU). The particularly preferred solvent is N,N-dimethylacetamide. The reaction is advantageously carried out at elevated temperature, preferably at from 120° to 170° C.

The thiolactone (IV) can be separated off from the salt present in the reaction mixture in the conventional manner by the addition of water and extraction with a non-polar solvent, such as, dichloromethane, and be isolated by fractional distillation or simple distilling off of the solvent.

The thiolactone (IV) is subsequently reacted with a nucleophile (V), with the lactone ring being opened and, depending on the nucleophile used, the γ-mercapto-carboxylic acid (I, $R^3$ is OH) or an ester or amide being formed.

Suitable nucleophiles (V) are, in accordance with the above definition of $R^3$, water or $OH^-$ from strong bases, such as, alkali or alkaline earth metal hydroxides, for example, LiOH, NaOH, KOH, Ca(OH)$_2$, Ba(OH)$_2$ or quaternary ammonium hydroxides. Preference is given to using alkali metal hydroxides. In the reaction with a strong base, the corresponding salt of the γ-mercaptocarboxylic acid is formed. This can be isolated as such or be converted into the free γ-mercaptocarboxylic acid by the addition of a strong acid. If the strong base is used in excess, the dianion of the γ-mercaptocarboxylic acid (with deprotonated mercapto group) can also be formed.

Further suitable nucleophiles are aliphatic ($R^3$ is $C_1$–$C_6$-alkoxy) and alicyclic ($R^3$ is cycloalkyloxy) alcohols, such as, methanol, ethanol, propanol, butanol, pentanol, hexanol, isopropanol, sec-butanol, tert-butanol, isobutanol, isopentanol, cyclopentanol or cyclohexanol. Preference is given to using $C_1$–$C_6$-alkanols or the corresponding alkoxides. Likewise suitable are phenols ($R^3$ is aryloxy), such as, phenol, naphthols, chlorophenols, cresols or xylenols, or arylalkanols ($R^3$ is aralkoxy), such as, benzyl alcohol, phenethyl alcohol or 3-phenyl-1-propanol.

A further class of nucleophiles (V) which can be used in the process of the invention are nitrogen bases, namely, ammonia ($R^3$ is $NH_2$), primary amines ($R^3$ is $NHR^4$) and secondary amines ($R^3$ is $NR^4R^5$). Suitable primary amines are alkylamines ($R^4$ is $C_1$–$C_6$alkyl), such as, methylamine, ethylamine, propylamine, butylamine or isopropylamine, and also cycloalkylamines ($R^4$ is cycloalkyl), such as, cyclohexylamine, aromatic amines ($R^4$ is aryl), such as, aniline or aniline substituted on the phenyl ring, or arylkylamines, such as, benzylamine or phenylethylamines. Suitable secondary amines are those having any combinations of the substituents specified above, for the primary amines, on the nitrogen, for example, dialkylamines, dicycloalkylamines, arylalkylamines, diarylamines and also cyclic amines, such as, pyrrolidine [$R^4$, $R^5$ is —$(CH_2)_4$—], piperidine [$R^4$, $R^5$ is —$(CH_2)_5$— ] or morpholine [$R^4$, $R^5$ is —$(CH_2)_2$—O—$(CH_2)_2$—]. Preferred nitrogen bases are ammonia and primary amines of the group $C_1$–$C_6$-alkylamines, the cycloalkylamines, the arylamines or the aralkylamines.

The reaction can be carried out under basic conditions, with, if desired, reaction being with the anion of the nucleophile used, i.e., a hydroxide, alkoxide or amide ion. For example, an alkali metal alkoxide in the corresponding alcohol (e.g., sodium methoxide in methanol) can be used to prepare the corresponding ester.

The reaction with water or alcohols can also be carried out with acid catalysis, thus, for example, $BF_3$ in methanol gives the methyl ester.

The following examples serve to clarify the procedure of the process of the invention and the preparation of the thiolactones of the invention.

EXAMPLE 1

5-Thiaspiro[2.4]heptan-6-one[IV, $R^1$, $R^2$=—$(CH_2)_2$—]

A 500 ml 4-neck flask fitted with mechanical stirrer, air condenser and internal thermometer was charged under a protective gas atmosphere with 41.23 g of 5-oxaspiro[2.4]heptan-6-one [II, $R^1$, $R_2$, =—$(CH_2)_2$—; prepared in accordance with European Published Patent Application No. 480717, "Method N"], 0.40 g of hydroquinone and 190.0 g of N,N-dimethylacetamide. After heating the contents of the flask to 155° C., 50.4 g of potassium thioacetate (purity>99%) was added. The mixture was stirred for 5 hours at 155°±1° C. After this time, the conversion (according to GC) was virtually quantitative. The reaction mixture was cooled to room temperature and admixed first with 2.3 g of concentrated acetic acid and subsequently with 185 ml of water. To remove the salts, the mixture was stirred for 15 minutes at room temperature, the phases were subsequently separated in a separating funnel and the aqueous phase was extracted two more times with 95 ml of dichloromethane each time. The combined organic phases were dried over sodium sulfate and freed of dichloromethane in a rotary evaporator. The residue was distilled at 5.1 mbar via a 30 cm packed column, with the N,N-dimethylacetamide initially passing over. The product having a purity of 99.8% (GC) subsequently passed over at 76° to 78° C. The yield of product was 93.0% of theory. Other data for the product was:

| | |
|---|---|
| $^1$H-NMR (CDCl$_3$, 300 MHz): δ | 0.76 (m, 4H) |
| | 2.49 (s, 2H) |
| | 3.22 (s, 2H) |
| IR (film, cm$^{-1}$) | 3001 (C—H); 1709 (vs, C = O); 1036 |

EXAMPLE 2

[1-(Mercaptomethyl)cyclopropyl]acetic acid [I, —$(CH_2)_2$—, $R^3$=OH]

At room temperature, 9.0 g ( 0.07 mol) of 5-thiaspiro[2.4]heptan-6-one [IV, $R^1$, $R^2$=—$(CH_2)_2$—; prepared in accordance with Example 1] was added in one portion under a protective gas to a solution of 3.7 g (91 mmol) of NaOH in 55 ml of water. The mixture was heated under reflux for 2.5 hours and subsequently cooled to <10° C. At this temperature, 15 ml of 6.07N hydrochloric acid was added dropwise over a period of 5 minutes with a white solid precipitating. This was dissolved by addition of 18 ml of methyl tert-butyl ether. The phases were separated and the aqueous phase was extracted two more times with 36 ml of methyl tert-butyl ether each time. The combined organic phases were dewatered by means of azeotropic distillation, with a further 10 ml of the ether being added during the course of the distillation. After the distillation was complete, the last traces of ether and water were removed in vacuo at 7.5 mbar and 62° C. After cooling, the vacuum was released by means of inert gas. The γ-mercapto acid was obtained as a colorless crystalline solid which, owing to its sensitivity to oxidation, has to be stored under inert gas. The yield of product was 9.8 g, which corresponds to 95% of theory. The product had a melting point of 42.5° to 43.8° C. Other data for the product was:

| | |
|---|---|
| $^1$H-NMR (CDCl$_3$, 300 MHz): δ | 0.55–0.68 (m, 4H) |
| | 1.38 (t, 1H) |
| | 2.54 (s, 2H) |
| | 2.65 (d, 2H) |
| IR (film on NaCl, cm$^{-1}$) | 3077.4, 3037.6 (C—H); 1705.5 (vs, C = O); 2570 (m, S—H). |

For further characterization, the corresponding disulfide was prepared:

[1- (1- Carboxymethylcyclopropylmethyldisulfanylmethyl)-cyclopropyl]acetic acid

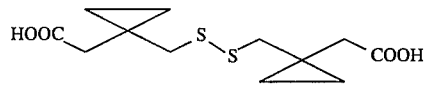

In a manner similar to the above procedure, 4.6 g (34.4 mmol) of 5-thiaspiro[2.4]heptan-6-one (95.5% pure) was hydrolyzed with 1.8 g (44.7 mmol) of sodium hydroxide. To the reaction mixture, cooled to 20° to 25° C., a solution of 6.0 g of potassium iodide and 4.4 g of iodine in 20 ml of water was added in small portions, so that towards the end of the addition the suspension was still slightly brown in color. The suspension was stirred for a further period of about 30 minutes at room temperature and subsequently decolorized with a few drops of aqueous sodium pyrosulfite solution. The reaction mixture was extracted with 200 ml of diethylether. The organic phase was dried over sodium sulfate, filtered and evaporated on a rotary evaporator. The remaining white solid was dried in a water pump vacuum at 60° C. and recrystallized from ethyl acetate. The disulfide product had a melting point of 135.5° to 136.2° C. Other data for the disulfide product was:

| | |
|---|---|
| $^1$H-NMR (DMSO-d$_6$, 400 MHz): δ | 0.6 (m, 8H) |
| | 2.3 (s, 4H) |
| | 2.9 (s, 4H) |
| | 12.05 (br · s, 2H) |

EXAMPLE 3

4,4-Dimethyldihydrothiophen-2-one (IV, $R^1$=$R^2$=$CH_3$)

In a manner similar to Example 1, 2.6 g of 4,4-dimethyldhydro-2(3H)-furanone (II, $R^1$=$R^2$=$CH_3$) was reacted at 160° C. with 3.1 g of potassium thioacetate in the presence of 22 mg of hydroquinone in 5.0 g of N,N-dimethylacetamide. After a reaction time of 7 hours, the conversion was 98.5% (GC). After working up in a manner similar to Example 1 and distillation via a small column, the thiolactone was obtained in a yield of 88.3% of theory and had a purity of 96.7% (GC). Other data for the product was:

| $^1$H-NMR (CDCl$_3$): δ | 1.27 (s, 6H) |
| --- | --- |
| | 2.40 (s, 2H) |
| | 3.19 (s, 2H) |

EXAMPLE 4

Methyl 3,3-dimethyl-4-mercaptobutyrate (I, $R^1=R^2=CH_3$, $R_3=OCH_3$)

4.0 g of 4,4-dimethyldihydrothiophen-2-one (96.7% pure, prepared in accordance with Example 3) was dissolved in 5 ml of methanol, admixed with 6.5 g of a 25% strength methanolic sodium methoxide solution while excluding moisture and subsequently heated under reflux for 2.5 hours. The methanol was subsequently distilled off in vacuo on a rotary evaporator and the residue was admixed with 2 ml of water and 1.8 g of acetic acid. The mixture thus obtained was extracted with 10 ml of dichloromethane and the extract was dried using sodium sulfate. The crude product obtainable by distilling off the dichloromethane contained 83.4% of the title substance besides 6.7% of starting material (GC). Data concerning the product was:

| $^1$H-NMR (CDCl$_3$): δ | 1.07 (s, 6H) |
| --- | --- |
| | 1.45 (t, 1H) |
| | 2.46 (s, 2H) |
| | 2.59 (d, 2H) |
| | 3.68 (s, 3H) |

EXAMPLE 5

[1—(Mercaptomethyl)cyclopropyl]acetic acid, lithium salt 0.63 g of lithium hydroxide monohydrate was dissolved in a mixture of 8.5 ml of water and 4.1 g of methanol and to this solution was added 1.9 g (15 mmol) of 5-thiaspiro [2.4]heptan-6-one (prepared in accordance with Example 1). The mixture was boiled under reflux for 3 hours, with the two phases initially present becoming an almost homogeneous solution. When residual starting material could no longer be detected by GC, the reaction mixture was evaporated at 70° C. in a water pump vacuum and the solid white residue was dried in vacuo at this temperature. For purification, the dried product was suspended in 10 ml of dichloromethane and, after stirring for 30 minutes at room temperature, was filtered off. After drying at 40° C. in vacuo, a white crystalline powder was obtained. The yield of the product was 1.9 g, which corresponds to 85% of theory. Other data concerning the product was:

| $^1$H-NMR[D$_2$O, internal standard 3-(tri-methylsilyl) propionic acid-d$_4$, sodium salt]: δ | 0.48–0.59 (m, 4H) |
| --- | --- |
| | 2.32 (s, 2H) |
| | 2.59 (s, 2H) |
| $^{13}$C-NMR (D$_2$O): δ | 15.42 |
| | 22.92 |
| | 35.63 |
| | 45.24 |
| | 184.44 |
| Elementary analysis (ICP) | Found Li 5.22% |
| | Calc. Li 4.56% |

EXAMPLE 6

N-Benzyl-[1-(mercaptomethyl)cyclopropyl]acetamide [I, $R^1$, $R^2$=—(CH$_2$)$_2$—, $R_3$=NHCH$_2$C$_6$H$_5$]

In 2.5 g of dioxane, 0.64 g (5 mmol) of 5-thiaspiro[2.4]-heptan-6-one (prepared in accordance with Example 1) and the equimolar amount of benzylamine was heated under reflux for 22.5 hours under protective gas. The dioxane colorless viscous oil slowly crystallized at 4° C. after the addition of a little petroleum ether to give fine needles. The yield of the product was 1.1 g, which corresponds to 91% of theory. Other data concerning the product was:

| $^1$H-NMR (CDCl$_3$): δ | 0.52–0.68 (m, 4H) |
| --- | --- |
| | 1.40 (t, 1H) |
| | 2.37 (s, 2H) |
| | 2.59 (d, 2H) |
| | 4.45 (d, 2H) |
| | 6.18 (br · s, 1H) |
| | 7.23–7.41 (m, 5H) |

EXAMPLE 7

[1-(Mercaptomethyl)cyclopropyl]acetamide [I, $R^1$, $R^2$=—(CH$_2$)$_2$—, $R^3$=NH$_2$]

A gentle stream of ammonia was passed into a solution of 5 g (39 mmol) of 5-thiaspiro [2.4]heptan-6-one (prepared in accordance with Example 1) in 50 ml of N,N-dimethylacetamide at 50° to 52° C. for 15 hours. The solvent was distilled out of the yellow reaction mixture in vacuo, with the product crystallizing out. For purification, it was recrystallized from acetone nitrile, with practically colorless crystals being obtained. The product had a melting point of 130° to 133.2° C. Other data concerning the product was:

| $^1$H-NMR (CDCl$_3$): δ | 0.42–0.58 (m, 4H) |
| --- | --- |
| | 2.18 (s, 2H) |
| | 2.16 (t, 1H) |
| | 6.76 (br · s, 2H) |

EXAMPLE 8

Methyl [1-(mercaptomethyl)cyclopropyl]acetate [I, $R^1$, $R^2$=—(CH$_2$)$_2$—, $R^3$ =OCH$^3$]

1.2 g of 5-thiaspiro[2.4]heptan-6-one (prepared in accordance with Example 1) was dissolved in 5 ml of methanol and admixed with 10 drops of a 1.3M solution of boron trifluoride diethyl ether adduct. The mixture was heated while excluding moisture for 22 hours in a closed tube and subsequently allowed to stand overnight at room temperature. GC analysis indicated a conversion of 94.2%. The produce was not isolated, but identified in the reaction mixture by means of $^1$H-NMR. The data thereof was:

| $^1$H-NMR (CDCl$_3$): δ | 0.49–0.65 (m, 4H) |
| --- | --- |
| | 1.38 (t, 1H) |
| | 2.50 (s, 2H) |
| | 2.64 (d, 2H) |
| | 3.68 (s, 3H) |

What is claimed is:
1. A process for preparing a γ-mercaptocarboxylic acid derivative of the formula:

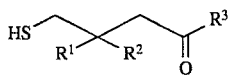

wherein $R^1$ and $R^2$ are either, independently of one another, hydrogen, $C_1$–$C_6$-alkyl or aralkyl or together are a —$(CH_2)_n$-group having n being an integer of 2 to 5, $R^3$ is hydroxy, $C_1$–$C_6$-alkoxy, cycloalkyloxy, aryloxy or aralkyloxy, or a salt thereof, comprising: reacting a γ-lactone of the formula:

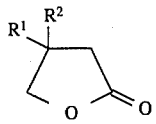

wherein $R^1$ and $R^2$ are as defined above, with a thiocarboxylate of the formula:

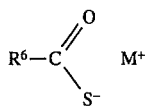

wherein $R^6$ is a $C_1$–$C_6$-alkyl group or a phenyl group and M is an alkali metal, in a polar solvent to give the corresponding thiolactone of the formula:

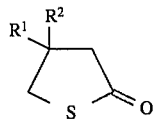

wherein $R^1$ and $R^2$ are as defined above, and subsequently reacting the thiolactone with a nucleophile of the formula:

$R^3H$   V wherein $R^1$ and $R^2$ are as defined above, or the corresponding anion:

$(R^3)^-$   V' to give the γ-mercaptocarboxylic acid derivative of formula I or a corresponding salt thereof.

2. The process according to claim 1 wherein the polar solvent used for the reaction of the γ-lactone with the thiocarboxylate is a polar aprotic solvent selected from the group consisting of dimethyl sulfoxide, sulfolane, N-methylpyrrolidone, N,N-dimethylformamide, N,N-dimethylacetamide and 1,3-dimethyl-3,4,5,6-tetrahydro-2(1H)-pyrimidinone.

3. The process according to claim 2 wherein the polar solvent used for the reaction of the γ-lactone with the thiocarboxylate is N,N-dimethylacetamide and the reaction is carried out at from 120° to 170° C.

4. The process according to claim 3 wherein the thiocarboxylate is potassium thioacetate.

5. The process according to claim 4 wherein a $C_1$–$C_6$-alkanol is used as the nucleophile $R^3H$ in the presence of boron trifluoride as a catalyst.

6. The process according to claim 4 wherein the nucleophile $(R^3)^-$ is the hydroxide ion from an alkali metal hydroxide.

7. The process according to claim 4 wherein the nucleophile $(R^3)^-$ is the alkoxide ion from a $C_1$–$C_6$-alkanol.

8. The process according to claim 1 wherein the polar solvent used for the reaction of the γ-lactone with the thiocarboxylate is carried out at from 120° to 170° C.

9. The process according to claim 1 wherein the thiocarboxylate is potassium thioacetate.

10. The process according to claim 1 wherein a $C_1$–$C_6$-alkanol is used as the nucleophile $R^3H$ in the presence of boron trifluoride as a catalyst.

11. The process according to claim 1 wherein the nucleophile $(R^3)^-$ is the hydroxide ion from an alkali metal hydroxide.

12. The process according to claim 1 wherein the nucleophile $(R^3)^-$ is the alkoxide ion from a $C_1$–$C_6$-alkanol.

13. A process for preparing a γ-mercaptocarboxylic acid derivative of the formula:

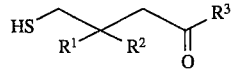

wherein $R^1$ and $R^2$ are either, independently of one another, hydrogen, $C_1$–$C_6$-alkyl or aralkyl or together are a —$(CH_2)_n$-group having n being an integer of 2 to 5, $R^3$ is —$NR^6R^5$ and $R^4$ and $R^5$ are either, independently of one another, hydrogen, $C_1$–$C_6$-alkyl, cycloalkyl, aryl or aralkyl, or $R^4$ and $R^5$ together are a —$(CH_2)_4$—, —$(CH_2)_5$— or —$(CH_2)_2$—O—$(CH_2)_2$— group, or a salt whereof, comprising: reacting a γ-lactone of the formula:

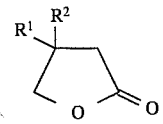

wherein $R^1$ and $R^2$ are as defined above, with a thiocarboxylate of the formula:

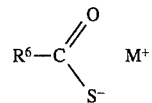

wherein $R^1$ is a $C_1$–$C_6$-alkyl group or a phenyl group and M is an alkali metal, in a polar solvent to give the corresponding thiolactone of the formula:

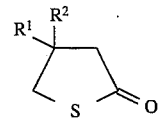

wherein $R^1$ and $R^2$ are as defined above, and subsequently reacting the thiolactone with a nucleophile of the formula:

$R^3H$   V wherein $R^1$ and $R^2$ are as defined above, or the corresponding anion:

$(R^3)^-$   V' to give the γ-mercaptocarboxylic acid derivative of formula I or a corresponding salt thereof.

14. The process according to claim 13 wherein the polar solvent used for the reaction of the γ-lactone with the thiocarboxylate is a polar aprotic solvent selected from the group consisting of dimethyl sulfoxide, sulfolane, N-methylpyrrolidone, N,N-dimethylformamide, N,N-dimethylacetamide and 1,3-dimethyl-3,4,5,6-tetrahydro-2(1H)-pyrimidinone.

15. The process according to claim 14 wherein the polar solvent used for the reaction of the γ-lactone with the thiocarboxylate is N,N-dimethylacetamide and the reaction is carried out at from 120° to 170° C.

16. The process according to claim 15 wherein the thiocarboxylate is potassium thioacetate.

17. The process according to claim 16 wherein the nucleophile $R^3H$ is ammonia.

18. The process according to claim 16 wherein the nucleophile $R^3H$ is an amine selected from the group consisting of $C_1$–$C_6$ alkylamines, the cycloalkylamines, the arylamines and the aralkylamines.

19. The process according to claim 13 wherein the polar solvent used for the reaction of the γ-lactone with the thiocarboxylate is carried out at from 120° to 170° C.

20. The process according to claim 13 wherein the thiocarboxylate is potassium thioacetate.

21. The process according to claim 13 herein the nucleophile $R^3H$ is ammonia.

22. The process according to claim 13 wherein the nucleophile $R^3H$ used is an amine selected from the group consisting of $C_1$–$C_6$ alkylamines, the cycloalkylamines, the arylamines and the aralkylamines.

23. The process according to claim 13 wherein $R^3$ is hydroxy.

24. The process according to claim 20 wherein the γ-mercaptocarboxylic acid derivative of formula I is in salt form.

* * * * *